(12) United States Patent
Yang et al.

(10) Patent No.: US 8,048,149 B2
(45) Date of Patent: Nov. 1, 2011

(54) INTRALUMINAL STENT INCLUDING THERAPEUTIC AGENT DELIVERY PADS, AND METHOD OF MANUFACTURING THE SAME

(75) Inventors: Linda Yang, Healdsburg, CA (US); Zhan Zhang, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 213 days.

(21) Appl. No.: 11/124,685

(22) Filed: May 9, 2005

(65) Prior Publication Data

US 2005/0256564 A1    Nov. 17, 2005

Related U.S. Application Data

(60) Provisional application No. 60/570,913, filed on May 13, 2004.

(51) Int. Cl.
*A61F 2/06* (2006.01)
(52) U.S. Cl. ............. 623/1.42; 623/1.11; 623/1.13; 623/1.34
(58) Field of Classification Search ............ 623/1.11, 623/1.13, 1.38, 1.39, 1.4, 1.42–1.44, 1.46, 623/1.12, 1.23, 1.34
See application file for complete search history.

(56) References Cited

U.S. PATENT DOCUMENTS

| | | | |
|---|---|---|---|
| 4,464,176 A | | 8/1984 | Wijayarathna |
| 5,441,515 A | * | 8/1995 | Khosravi et al. ............. 623/1.15 |
| 5,674,242 A | * | 10/1997 | Phan et al. .................... 606/198 |
| 5,704,926 A | | 1/1998 | Sutton |
| 5,951,458 A | * | 9/1999 | Hastings et al. .................. 600/3 |
| 6,221,099 B1 | * | 4/2001 | Andersen et al. ............ 623/1.15 |
| 6,517,889 B1 | | 2/2003 | Jayaraman |
| 6,530,950 B1 | * | 3/2003 | Alvarado et al. ............ 623/1.13 |
| 6,774,278 B1 | * | 8/2004 | Ragheb et al. ................. 623/1.1 |
| 2001/0020181 A1 | * | 9/2001 | Layne .......................... 623/1.13 |
| 2003/0181973 A1 | * | 9/2003 | Sahota ......................... 623/1.15 |
| 2003/0216803 A1 | * | 11/2003 | Ledgerber ................. 623/1.13 |

* cited by examiner

*Primary Examiner* — David Isabella
*Assistant Examiner* — Suba Ganesan

(57) ABSTRACT

An intraluminal stent, an intraluminal stent delivery system, and a method of manufacturing an intraluminal stent. The stent comprises a body and at least one pad operably attached to the stent body. The pad includes at least one therapeutic agent disposed thereon. The delivery system comprises a catheter and the stent disposed on the catheter. The manufacturing method includes providing a stent including a body, and at least one pad. The pad is operably attached to the stent body. The pad is treated with at least one therapeutic agent.

28 Claims, 3 Drawing Sheets

INTRALUMINAL STENT INCLUDING THERAPEUTIC AGENT DELIVERY PADS, AND METHOD OF MANUFACTURING THE SAME

RELATED APPLICATIONS

This application claims the benefit of U.S. Provisional Patent Application 60/570,913 filed May 13, 2004.

TECHNICAL FIELD OF THE INVENTION

The present invention relates generally to the field of implantable medical devices. More particularly, the invention relates to an intraluminal stent including therapeutic agent delivery pads, and a method of manufacturing the same.

BACKGROUND OF THE INVENTION

Balloon angioplasty has been used for the treatment of narrowed and occluded blood vessels. A frequent complication associated with the procedure is restenosis, or vessel re-narrowing. Within 3 to 6 months of angioplasty, restenosis occurs in almost 50 percent of patients. To reduce the incidence of re-narrowing, several strategies have been developed. Implantable devices, such as stents, have been used to reduce the rate of angioplasty-related restenosis by about half. The use of such intraluminal devices has greatly improved the prognosis of these patients. Nevertheless, restenosis remains a formidable problem associated with the treatment of narrowed blood vessels.

Restenosis associated with interventional procedures such as balloon angioplasty may occur by at least two mechanisms: thrombosis and intimal hyperplasia. During angioplasty, a balloon is inflated within an affected vessel, thereby compressing the blockage and imparting a significant force, and subsequent trauma, upon the vessel wall. The natural anti-thrombogenic lining of the vessel lumen may become damaged, thereby exposing thrombogenic cellular components, such as matrix proteins. The cellular components, along with the generally antithrombogenic nature of any implanted materials (e.g., a stent), may lead to the formation of a thrombus, or blood clot. The risk of thrombosis is generally greatest immediately after the angioplasty.

A second mechanism of restenosis is intimal hyperplasia, or excessive tissue re-growth. The trauma imparted upon the vessel wall from the angioplasty is generally believed to be an important factor contributing to hyperplasia. This exuberant cellular growth may lead to vessel "scarring" and significant restenosis. The risk of hyperplasia-associated restenosis is usually greatest 3 to 6 months after the procedure.

Prosthetic devices, such as stents or grafts, may be implanted during interventional procedures such as balloon angioplasty to reduce the incidence of vessel restenosis. To improve device effectiveness, stents may be coated with one or more therapeutic agents providing a mode of localized drug delivery. The therapeutic agents are typically intended to limit or prevent the aforementioned mechanisms of restenosis. For example, antithrombogenic agents such as heparin or clotting cascade IIb/IIIa inhibitors (e.g., abciximab and eptifibatide) may be coated on the stent, thereby diminishing thrombus formation. Such agents may effectively limit clot formation at or near the implanted device. Some antithrombogenic agents, however, may not be effective against intimal hyperplasia. Therefore, the stent may also be coated with antiproliferative agents or other compounds to reduce excessive endothelial re-growth. Therapeutic agents provided as coating layers on implantable medical devices may effectively limit restenosis and reduce the need for repeated treatments.

Several strategies have been developed for coating one or more therapeutic agents onto the stent surface. Standard methods may include dip coating, spray coating, and chemical bonding. The therapeutic agent coating may be applied as a mixture, solution, or suspension of polymeric material and/or drugs dispersed in an organic vehicle or a solution or partial solution. Further, the coating may include one or more sequentially applied, relatively thin layers deposited in a relatively rapid sequence. The stent is typically in a radially expanded state during the application process. In some applications, the coating may include a composite initial tie coat, or undercoat, and a composite topcoat, or cap coat. The coating thickness ratio of the topcoat to the undercoat may vary with the desired effect and/or the elution system. Examples of various stent coating strategies are discussed in the background portion of U.S. Pat. No. 6,517,889 issued to Jayaraman.

Regardless of the strategy used to coat the stent, the coating material is generally deposited directly on the stent framework and joints. The material, especially when it is thicker, may serve to "stiffen" the stent structure. As such, the stent may not easily be able to move (e.g., bend and flex) when deployed within the vasculature. In some instances, problems may arise when the "stiffened" stent is deployed in a mobile vascular site (e.g., arm, leg, neck, etc.). The vascular endothelium may even sustain damage should the coated stent not move in compliance with the vessel. This may negate the beneficial effects of the coating and the stent itself. Therefore, it would be desirable to provide a strategy for delivering a therapeutic agent associated with a stent that would not restrain the movement of the stent.

Another shortcoming associated with some coated stents relates to the generally complex and time-consuming coating/layering process. The use of multiple layers and various coating geographies (i.e., coatings differentially positioned on the stent) may be expensive, time-consuming, and inefficient due to the elaborate coating machinery, step number, and complexity sometimes involved. The process may be further complicated for stent coatings including multiple drugs, polymers, and solvents, some of which may be immiscible and/or incompatible with one another. As such, it would be desirable to provide a relatively inexpensive and efficient strategy for delivering one or more therapeutic agents on a stent.

Yet another shortcoming associated with some coated stents relates to drug load. Many stents are constructed from a thin mesh framework and thus do not include a sufficiently large surface area to retain substantial amounts of therapeutic agent(s). Therefore, it would be desirable to provide a strategy for increasing the amount of therapeutic agent(s) carried by the stent.

Accordingly, it would be desirable to provide an intraluminal stent including therapeutic agent delivery pads, and a method of manufacturing the same, that would overcome the aforementioned and other disadvantages.

SUMMARY OF THE INVENTION

A first aspect according to the invention provides an intraluminal stent. The stent comprises a body and at least one pad operably attached to the body. The pad includes at least one therapeutic agent disposed thereon.

A second aspect according to the invention provides an intraluminal stent delivery system. The system comprises a catheter and a stent disposed on the catheter. The stent comprises a body and at least one pad operably attached to the body. The pad includes at least one therapeutic agent disposed thereon.

A third aspect according to the invention provides a method of manufacturing an intraluminal stent. The method includes providing a stent including a body, and at least one pad. The pad is operably attached to the stent body. The pad is treated with at least one therapeutic agent.

The foregoing and other features and advantages of the invention will become further apparent from the following detailed description of the presently preferred embodiments, read in conjunction with the accompanying drawings. The detailed description and drawings are merely illustrative of the invention, rather than limiting, the scope of the invention being defined by the appended claims and equivalents thereof.

DESCRIPTION OF THE PRESENTLY PREFERRED EMBODIMENTS

Figure 1:
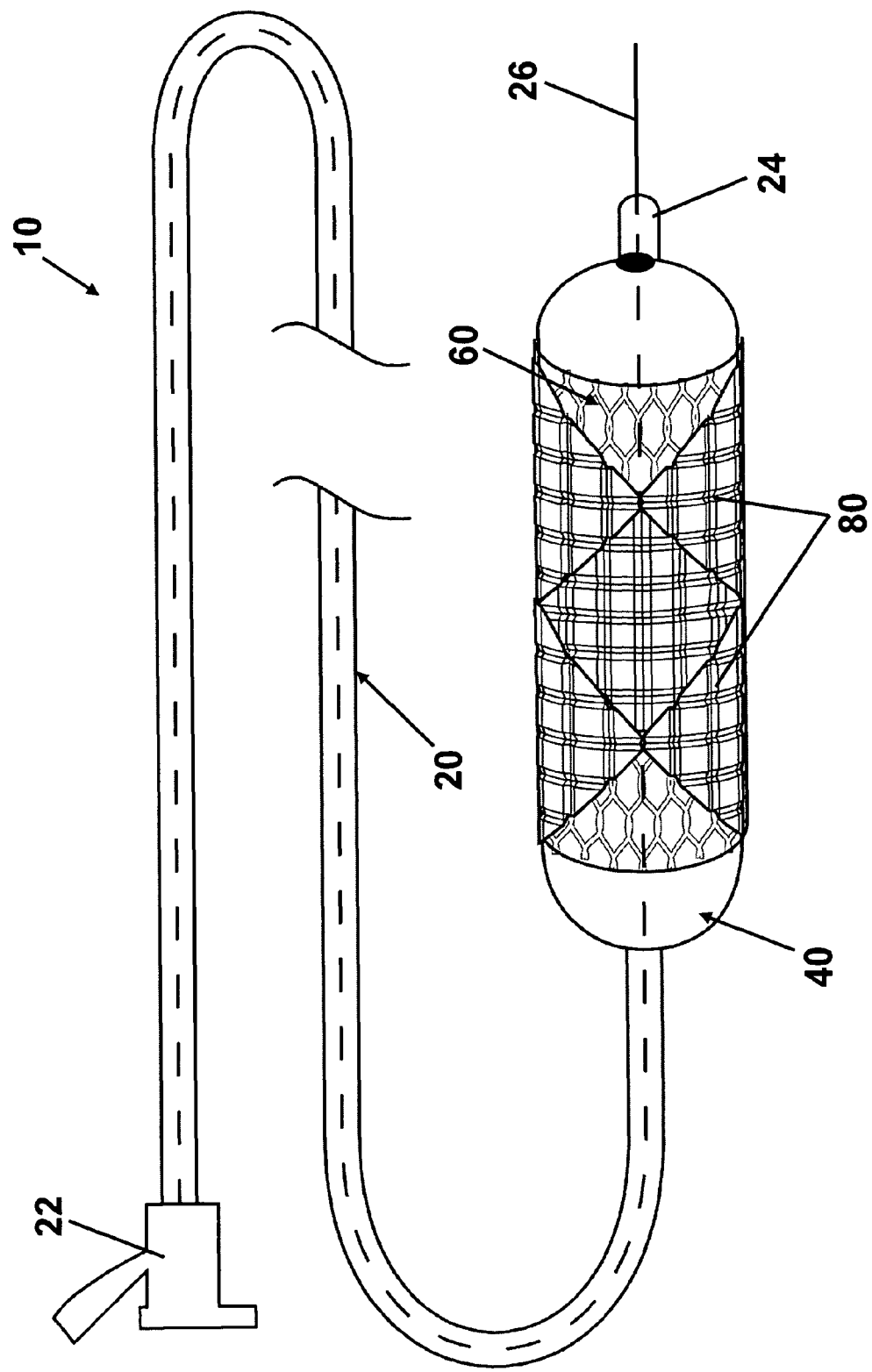
FIG. 1 is a perspective view of an intraluminal stent delivery system including a stent mounted on a balloon catheter, in accordance with one embodiment of the present invention.

Referring to the drawings, wherein like reference numerals refer to like elements, FIG. 1 is a perspective view of an intraluminal stent delivery system (not to scale) in accordance with one embodiment of the present invention and shown generally by numeral 10. System 10 includes a catheter 20, a balloon 40 operably attached to the catheter 20, and a stent 60 disposed on the balloon 40. Stent 60 includes a stent body 62, at least one pad 80, and at least one therapeutic agent (not shown) disposed on the pad 80.

Balloon 40, shown in a collapsed state, may be any variety of balloon capable of expanding stent 60. Balloon 40 may be manufactured from any sufficiently elastic material such as polyethylene, polyethylene terephthalate (PET), nylon, or the like. Stent 60, which is also shown in a collapsed state, may be expanded in sympathy with balloon 40. Stent 60 comprises a plurality of pads 80 including at least one therapeutic agent operably attached to body 62 of stent 60. The terms "catheter" and "stent," as used herein, may include any number of intravascular and/or implantable prosthetic devices capable of performing the functions according to the invention and are not limited to the examples provided herein.

Catheter 20 may comprise an elongated tubular member having substantially circular (in cross-section) inside and outside walls that are preferably substantially smooth. Catheter 20 may be secured at its proximal end to a suitable Luer fitting 22 and may include a distal rounded end 24 to reduce harmful contact with a vessel. Catheter 20 may be manufactured substantially from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax®, Vestamid®, Tecoflex®, Halar®, Hyflon®, Pellathane®, combinations thereof, and the like. Catheter 20 may include an aperture formed therethrough allowing it to be advanced over a pre-positioned guidewire 26. Catheter 20 may further include a drug delivery element (not shown) for delivering treatment compounds to the vessel during stent deployment. In one embodiment, the drug delivery element may include at least one elongated tube positioned within catheter 20. As such, additional drugs may be administered to the patient during the stent deployment procedure.

Catheters typically are composed of tubes made of one or more polymeric materials, sometimes in combination with metallic reinforcement. In some applications (such as treating smaller, more tortuous arteries), it is desirable to construct the catheter from very flexible materials to facilitate advancement of the catheter into such difficult access locations. Catheters are known in the art that provide different regions of flexibility (e.g., a stiffer proximal section and a more flexible distal section).

Examples of such catheters include U.S. Pat. No. 4,464,176 issued to Wijayarathna, which describes a catheter made of two layers of tubing, one of the layers being more flexible than the other and extending distally beyond the end of the other layer by a considerable distance. U.S. Pat. No. 5,704,926 issued to Sutton describes a catheter that includes inner and outer tubular layers, and a continuous helical wire coil disposed between the tubular layers along substantially the entire length of the catheter. The wire coil is constructed to provide regions of differing flexibility to enhance catheter trackability and pushability.

In another embodiment (not shown), the catheter may include a lumen formed therein for deploying a self-expanding stent as known in the art and discussed below. For such stent delivery systems, a balloon is typically not required to deploy the stent.

Figure 2:
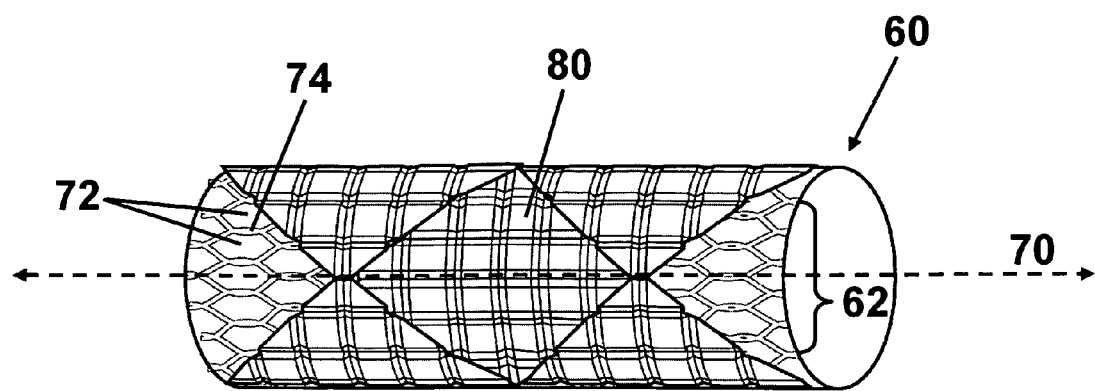
FIG. 2 is a perspective view of the stent of FIG. 1 shown in a compressed state.

Stent 60, which is shown in greater detail in FIG. 2, may comprise any variety of implantable prosthetic devices as known in the art. Stent body 62 may be manufactured from a skeletal framework or mesh of material forming a tube-like structure and may be capable of self-expanding or being expanded by another device such as a balloon. In one embodiment, stent body 62 may include a plurality of identical cylindrical segments 64 placed end to end. Those skilled in the art will recognize that the number of segments may vary and that numerous other stents, grafts, and implantable prosthetic devices may be adapted for use with the present invention; the described stent is provided merely as an example.

Stent body 62 may be generally tubular, defining a passageway extending along a longitudinal axis 70. Stent body 62 may include the plurality of cylindrical segments 64 arranged successively along the longitudinal axis 70. Each of cylindrical segments 64 may have a length along the longitudinal axis 70 and may include a plurality of O-shaped elements 66. The O-shaped elements 66 may be staggered along the longitudinal axis 70 about the perimeter or circumference of the cylindrical segments 64. The O-shaped elements 66 may be connected to each other by a tie member 68 that is attached to center sections of each of the O-shaped elements 66.

Figure 3:
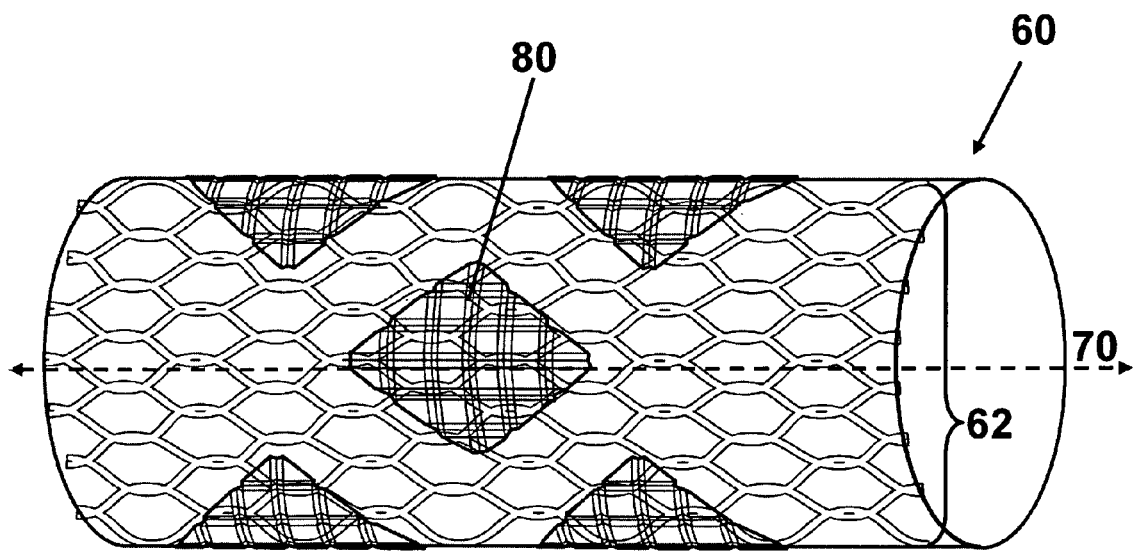
FIG. 3 is a perspective view of the stent of FIG. 1 shown in an expanded state.

In FIG. 3, stent 60 is shown in an expanded state in which the cylindrical segments 64 have been expanded radially outward from the longitudinal axis 70 and the pads 80 are spaced apart one from another. Stent 60 may be compressed into a smaller diameter (i.e., when "mounted" on a balloon as shown in FIG. 1 or "loaded" within a catheter lumen) for delivery within a vessel lumen, at which point stent 60 may be expanded to provide support to the vessel. As previously described, stent 60 may be designed to be expanded by a balloon or some other device, and stent body 62 may be manufactured from an inert, biocompatible material with high corrosion resistance. The biocompatible material should ideally be plastically deformed at low-moderate stress levels. Alternatively, stent 60 may be of the self-expanding variety and stent body 62 may be manufactured from, for example, nickel titanium alloys and/or other alloys that exhibit superlastic behavior (i.e., capable of significant distortion without plastic deformation). Suitable materials for stents include, but are not limited to, tantalum, stainless steel, titanium ASTM F63-83 Grade 1, niobium or high carat gold K 19-22. Furthermore, the stent body 62 material may include any number of other metallic and/or polymeric biocompatible materials recognized in the art for such devices.

In one embodiment, the pads 80 may be sized substantially smaller than and positioned on an outer surface of stent body 62. However, as shown in FIGS. 1 and 2, the pads 80 may collectively cover the entire outer surface of stent 60 while it is in the compressed configuration. When stent 60 expands, as shown in FIG. 3, the pads 80 may then move apart from one another comprising a smaller proportion of the stent outer surface. Preferably, the pads 80 are operably attached to the stent in a manner that does not greatly interfere with the stent expansion (i.e., free of the stent body joints). In the example as shown in FIGS. 1-3, the pads 80 can be generally diamond shaped with two opposite corners aligned parallel to the longitudinal axis 70.

Figure 4B:
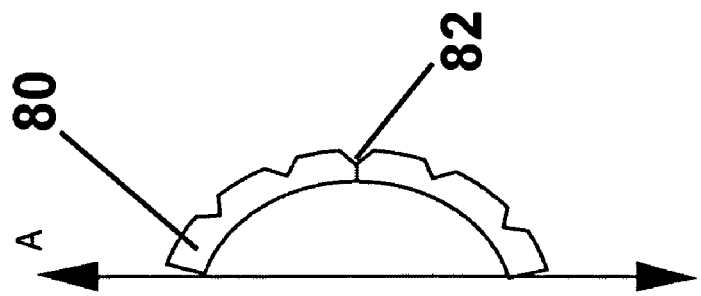
FIGS. 4A and 4B are detailed front and cross-sectional views of a stent pad shown in FIGS. 1-3.
Figure 4A:
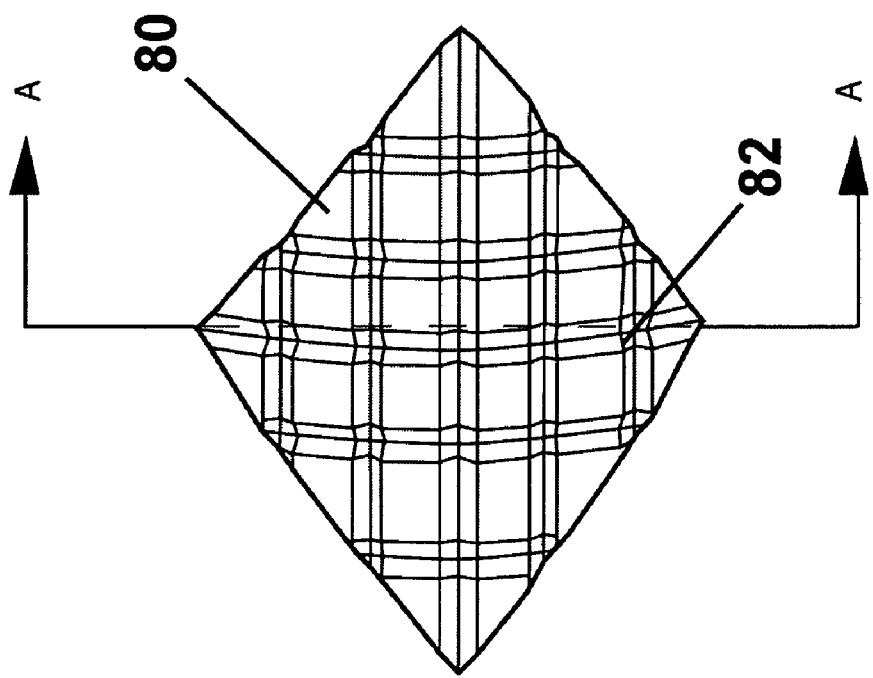

FIGS. 4A and 4B are a detailed front view of pad 80 and a cross-sectional view of pad 80 along lines A-A. As shown, pad 80 is generally shaped to correspond to a contour of stent body 62 (i.e., has a complementary curvature). This reduces the overall size and bulk of stent 60. Pad 80 may be operably attached to stent body 62 with at least one attachment, such as a weld, an adhesive, a clip, a hook, a tie, and the like. In one embodiment, each pad 80 is attached to stent body 62 with a single laser spot-weld. This provides a secure, quick, and inexpensive attachment option.

In one embodiment, both pad 80 and stent body 62 are manufactured from a like material, both thereby exhibiting like expansion and compression characteristics. Those skilled in the art will recognize that the pad 80 material may vary. Pad 80 generally functions to retain one or more therapeutic agents and may, therefore, comprise an absorbent material. The therapeutic agents may be retained on or within pad 80 as one or more coating layers. Pad 80 may include one or more grooves 82 formed therein. In the present embodiment, the grooves are provided in a cross-hatch type pattern. Numerous other patterns, designs, and geometries may be used. Grooves 82 may advantageously allow pad 80 to move (e.g., bend and flex) along with stent body 62. Unlike thick coatings layered directly onto a stent body, the pad generally does not overly restrain movement of the stent, thereby facilitating its deployment in mobile vascular sites. Grooves 82 may further provide an area where the therapeutic agent may be concentrated, thereby allowing additional quantities of an agent or additional agents to be included thereon.

In one embodiment, the therapeutic agent comprises a drug, a polymer, a solvent, a component thereof, a combination thereof, and the like. For example, the therapeutic agent may include a mixture of a drug and a polymer dissolved in a compatible liquid solvent as known in the art. Some exemplary drug classes that may be included with the pad are antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, (lipo)proteins, nitrates, nitric oxide releasing agents, vasodilators, virus-mediated gene transfer agents, agents having a desirable therapeutic application, and the like. Specific examples of drugs include abciximab; angiopeptin; colchicine; eptifibatide; heparin; hirudin; lovastatin; methotrexate; streptokinase; taxol; ticlopidine; tissue plasminogen activator; trapidil; urokinase; and growth factors VEGF, TGF-beta, IGF, PDGF, and FGF.

The polymer generally provides a matrix for incorporating the drug within the coating. Some exemplary biodegradable polymers that may be adapted for use with the present invention include, but are not limited to, polycaprolactone, polylactide, polyglycolide, polyorthoesters, polyanhydrides, poly (amides), poly(alkyl-2-cyanoacrylates), poly(dihydropyrans), poly(acetals), poly(phosphazenes), poly(dioxinones), trimethylene carbonate, polyhydroxybutyrate, polyhydroxyvalerate, their copolymers, blends, and copolymer blends, combinations thereof, and the like. Exemplary non-biodegradable polymers that may be adapted for use with the present invention may be divided into at least two classes. The first class includes hydrophobic polymers such as polyolefins, acrylate polymers, vinyl polymers, styrene polymers, polyurethanes, polyesters, epoxy, nature polymers, their copolymers, blends, and copolymer blends, combinations thereof, and the like. The second class includes hydrophilic polymers, or hydrogels, such as polyacrylic acid, polyvinyl alcohol, poly(N-vinylpyrrolidone), poly(hydroxy-alkylmethacrylate), polyethylene oxide, their copolymers, blends and copolymer blends, combinations of the above, and the like.

Some exemplary solvents that may be adapted for use with the present invention include, but are not limited to, acetone, ethyl acetate, tetrahydrofuran (THF), chloroform, N-methylpyrrolidone (NMP), and the like.

Those skilled in the art will recognize that the nature of the drug, polymer, and solvent may vary greatly, a therapeutic agent typically being formulated to achieve a given therapeutic effect such as limiting restenosis, thrombus formation, hyperplasia, etc. Once formulated, a therapeutic agent (mixture) may be applied to pad 80 by any of numerous strategies known in the art, including, but not limited to, spraying, dipping, rolling, nozzle injection, and the like. It will be recognized that the therapeutic agent may be alternatively layered, arranged, configured on/within the pad depending on the desired effect. Further, a single stent may include pads with varying therapeutic agents from one pad to the next. Once applied, the therapeutic agent may be dried (i.e., by allowing the solvent to evaporate) and, optionally, other layers added thereon.

Referring again to FIG. 1, stent 60 may be deployed at an appropriate site within a patient in a manner in accordance with the catheter design. For example, stent 60 may be expanded from a compressed configuration (as shown) to an expanded configuration by balloon catheter 20 or, alternatively, by a self-expanding mechanism. Stent positioning and deployment strategies and devices are known to those skilled in the art and may be adapted herewith. Once stent 60 is deployed, the pads may contact the vessel wall, and the catheter may be withdrawn from the patient. Pads 80 may continue to elute one or more drugs that typically have beneficial effects and/or minimize adverse effects on the patient. As a therapeutic agent is located on the pads and not the stent body, stent 60 may be free to move in response to vessel movements. Those skilled in the art will recognize that numerous elution kinetics and drug delivery profiles may additionally be provided with the pads.

While the embodiments of the invention disclosed herein are presently considered to be preferred, various changes and modifications can be made without departing from the spirit and scope of the invention. For example, the stent configuration is not limited to any particular stent design. In addition, the therapeutic agent composition and pad coating process may be varied while providing an effective drug-eluting stent. Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

The invention claimed is:

1. An intraluminal stent comprising:
   a body; and
   a plurality of pads operably attached to an outer surface of the body, the plurality of pads being disposed on the body to collectively form a continuous surface with the plurality of pads together covering the outer surface of the body when the body is in a compressed configuration and a spaced apart configuration having each of the plurality of pads spaced apart from each other of the plurality of pads when the body is in an expanded state, wherein each pad of the plurality of pads covers a plurality of stent elements; wherein each of the plurality of pads is generally diamond shaped with two opposite corners aligned parallel to a longitudinal axis of the body and wherein the pads include at least one therapeutic agent disposed thereon.

2. The stent of claim 1 wherein the plurality of pads is generally shaped to correspond to a contour of the body.

3. The stent of claim 1 wherein the plurality of pads comprises an absorbent material.

4. The stent of claim 1 wherein the plurality of pads is operably attached to the stent body with at least one attachment selected from a group consisting of a weld, an adhesive, a clip, a hook, and a tie.

5. The stent of claim 1 wherein each of the plurality of pads is sized substantially smaller than the stent body.

6. The stent of claim 1 wherein the plurality of pads comprises a plurality of coating layers.

7. The stent of claim 1 wherein the plurality of pads comprises at least one groove formed therein.

8. The stent of claim 7 wherein the therapeutic agent is positioned within the at least one groove.

9. The stent of claim 7 wherein the groove facilitates movement of the plurality of pads.

10. The stent of claim 1 wherein the therapeutic agent comprises at least one of a drug, a polymer, and a solvent.

11. The stent of claim 1 wherein the plurality of pads are spaced apart circumferentially in the spaced apart configuration.

12. An intraluminal stent delivery system comprising:
    a catheter; and
    stent disposed on the catheter, the stent comprising a body and a plurality of pads operably attached to the body; wherein the plurality of pads includes at least one therapeutic agent disposed thereon, the plurality of pads being disposed on an outer surface of the body to collectively form a continuous surface with the plurality of pads together covering the outer surface of the body when the body is in a compressed configuration and a spaced apart configuration where each of the plurality of pads is spaced apart from each other of the plurality of pads when the body is in an expanded state, wherein each pad of the plurality of pads covers a plurality stent elements and wherein each of the plurality of pads is generally diamond shaped with two opposite corners aligned parallel to a longitudinal axis of the body.

13. The system of claim 12 wherein the catheter includes a balloon operably attached to the catheter.

14. The system of claim 12 wherein the catheter includes a drug delivery element.

15. The system of claim 12 wherein the plurality of pads is generally shaped to correspond to a contour of the stent body.

16. The system of claim 12 wherein the plurality of pads comprises an absorbent material.

17. The system of claim 12 wherein the plurality of pads is operably attached to the stent body with at least one attachment selected from a group consisting of a weld, an adhesive, a clip, a hook, and a tie.

18. The system of claim 12 wherein each of the plurality of pads is sized substantially smaller than the stent body.

19. The system of claim 12 wherein the plurality of pads comprises a plurality of coating layers.

20. The system of claim 12 wherein the plurality of pads comprises at least one groove formed therein.

21. The system of claim 20 wherein the therapeutic agent is positioned within the at least one groove.

22. The system of claim 20 wherein the groove facilitates movement of the plurality of pads.

23. The system of claim 12 wherein the therapeutic agent comprises at least one of a drug, a polymer, and a solvent.

24. The stent of claim 12 wherein the plurality of pads are spaced apart circumferentially in the spaced apart configuration.

25. A method of manufacturing an intraluminal stent, the method comprising:
    providing a stent including a body;
    providing a plurality of pads;
    operably attaching the plurality of pads to an outer surface of the stent body, the plurality of pads being attached to the body to collectively form a continuous surface with the plurality of pads together covering the outer surface of the body when the body is in a compressed configuration and a spaced apart configuration where each of the plurality of pads is spaced apart from each other of the plurality of pads when the body is in an expanded state, wherein each pad of the plurality of pads covers a plurality of stent elements; wherein each of the plurality of pads is generally diamond shaped with two opposite corners aligned parallel to a longitudinal axis of the body and
    treating the plurality of pads with at least one therapeutic agent.

26. The method of claim 25 wherein treating the plurality of pads with at least one therapeutic agent comprises concentrating the therapeutic agent.

27. The method of claim 25 wherein treating the plurality of pads with at least one therapeutic agent comprises layering the therapeutic agent.

28. The method of claim 25 wherein treating the plurality of pads with at least one therapeutic agent comprises at least one of spraying the therapeutic agent and injecting the therapeutic agent.

* * * * *